(12) United States Patent
Durfee

(10) Patent No.: US 10,010,477 B2
(45) Date of Patent: Jul. 3, 2018

(54) PORTABLE RADIANT EXERCISE AND SAUNA TENT

(71) Applicant: Creatrix Solutions LLC, Kennewick, WA (US)

(72) Inventor: Eileen Durfee, Kennewick, WA (US)

(73) Assignee: CREATRIX SOLUTIONS LLC, Kennewick, WA (US)

(*) Notice: Subject to any disclaimer, the term of this patent is extended or adjusted under 35 U.S.C. 154(b) by 0 days.

(21) Appl. No.: 15/695,492

(22) Filed: Sep. 5, 2017

(65) Prior Publication Data
US 2017/0367929 A1 Dec. 28, 2017

Related U.S. Application Data

(63) Continuation-in-part of application No. PCT/IB2015/058785, filed on Nov. 13, 2015.
(Continued)

(51) Int. Cl.
*A61H 33/06* (2006.01)
*E04H 15/44* (2006.01)
(Continued)

(52) U.S. Cl.
CPC ......... *A61H 33/066* (2013.01); *A61N 5/0625* (2013.01); *E04H 15/12* (2013.01);
(Continued)

(58) Field of Classification Search
CPC ......... E04H 15/10; E04H 15/12; E04H 15/44; E04H 15/52; E04H 15/54; A61H 2201/0157; A61H 33/066; A47K 3/32
(Continued)

(56) References Cited

U.S. PATENT DOCUMENTS 1,425,391 A * 8/1922 La Munyon ........... A47K 11/02 4/460
1,925,815 A * 9/1933 Nicolson .................. E04H 6/02 135/119
(Continued)

FOREIGN PATENT DOCUMENTS

DE 10344800 A1 * 4/2005 ............... A61N 5/06

OTHER PUBLICATIONS 1 page Derwent English Abstract of KR 2016103732 A, Sep. 2016.*
1 page Clipped Image associated with Derwent Abstract of KR 2016103732 A, Sep. 2016.*

*Primary Examiner* — Robert Canfield

(57) ABSTRACT

A modular portable exercise and sauna tent is an apparatus that provides an enclosed phototherapeutic environment for a user. The size and shape of the apparatus is adjustable depending on the position of the user within the apparatus. The apparatus includes a scaffolding, a thermally insulative cover, and at least one heating lamp. The thermally insulative cover further includes a first panel, a second panel, and an overlay panel. The scaffolding defines an area of heat around the user. The thermally insulative cover encloses the defined area. The scaffolding further includes a first base frame, a second base frame, and a plurality of lateral posts, each of which are adjustable in length. The shapes of the first base frame and the second base frame are both adjustable. The apparatus preferably includes a flooring layer that provides comfort and protection for the user against the ground.

22 Claims, 22 Drawing Sheets

Related U.S. Application Data

(60) Provisional application No. 62/132,783, filed on Mar. 13, 2015.

(51) Int. Cl.
*E04H 15/12* (2006.01)
*A61N 5/06* (2006.01)

(52) U.S. Cl.
CPC ....... *E04H 15/44* (2013.01); *A61H 2033/061* (2013.01); *A61H 2201/0157* (2013.01); *A61H 2201/0161* (2013.01); *A61N 2005/0636* (2013.01); *A61N 2005/0659* (2013.01)

(58) Field of Classification Search
USPC ........ 135/91, 62, 115, 157, 900, 902; 4/527; 607/81
See application file for complete search history.

(56) References Cited

U.S. PATENT DOCUMENTS

| | | | | |
|---|---|---|---|---|
| 2,168,913 A * | 8/1939 | Middleton | ............... | E04H 15/00 135/118 |
| 2,511,452 A * | 6/1950 | Andersonan | .......... | E04H 15/001 135/117 |
| 3,271,786 A * | 9/1966 | Joy | ........................ | A61H 33/06 4/532 |
| 3,391,409 A * | 7/1968 | Gatley | .................. | A47K 3/325 4/599 |
| 4,077,418 A * | 3/1978 | Cohen | .................... | E04H 15/48 135/118 |
| 4,938,243 A * | 7/1990 | Foster | .................. | E04H 15/001 135/128 |
| 5,010,909 A * | 4/1991 | Cleveland | ............. | E04H 15/001 135/119 |
| 5,069,623 A * | 12/1991 | Peat | ......................... | G09B 1/06 434/260 |
| 5,133,378 A * | 7/1992 | Tanasychuk | .......... | E04H 15/001 135/148 |
| 5,216,948 A * | 6/1993 | Sheppard | ................. | A21D 8/04 126/281 |
| 5,377,711 A * | 1/1995 | Mueller | ................. | E04H 15/001 135/115 |
| 5,511,254 A * | 4/1996 | O'Brien | ................. | A61H 33/06 135/157 |
| 5,622,198 A * | 4/1997 | Elsinger | ................. | E04B 1/344 135/116 |
| 5,628,073 A * | 5/1997 | Popovich | .............. | A61H 33/06 135/115 |
| 5,884,647 A * | 3/1999 | Dwek | ..................... | E04H 15/52 135/144 |
| 5,920,927 A * | 7/1999 | Thomas | ................. | A47K 11/00 4/449 |
| 6,701,948 B2 * | 3/2004 | Jopp | ..................... | E04H 15/001 135/115 |
| 7,299,531 B2 * | 11/2007 | Staples | .................... | G01B 3/08 29/434 |
| D568,550 S * | 5/2008 | Totty | ............................ | D30/158 |
| D752,724 S * | 3/2016 | Coats | .......................... | D23/283 |
| 2006/0213546 A1* | 9/2006 | Mitsui | ..................... | E04H 15/42 135/121 |
| 2009/0308422 A1* | 12/2009 | Rizzotto | ................. | E04H 4/108 135/121 |
| 2016/0015597 A1* | 1/2016 | Richards | .............. | A61H 33/066 4/524 |
| 2016/0237714 A1* | 8/2016 | Tufto | .................... | E04H 15/001 |

* cited by examiner

PORTABLE RADIANT EXERCISE AND SAUNA TENT

The current application is a continuation-in-part (CIP) application of the Patent Cooperation Treaty (PCT) application PCT/IB2015/058785 filed on Nov. 13, 2015. The PCT application PCT/IB2015/058785 claims a priority to the U.S. Provisional Patent application Ser. No. 62/132,783 filed on Mar. 13, 2015.

FIELD OF THE INVENTION

The present invention relates generally to exercise tents. More specifically, the present invention is a portable radiant exercise and sauna tent. The present invention provides an enclosed space for which a user may receive phototherapy treatments.

BACKGROUND OF THE INVENTION

Exposure to light energy can trigger numerous biochemical reactions in organisms. Plant organisms use photosynthesis to convert light energy into the chemical energy. Humans utilize light energy for processes such as vision, vitamin D metabolism, and skin tanning, among many others. Such photo-biochemical reactions are dependent on the wavelength of the light. Moreover, different wavelengths yield different results. Treatments inducing photo-biochemical reactions, which feature exposure to daylight or to specific wavelengths of light, have come to be known as "phototherapy." Therapeutic gains achieved with various forms of phototherapy are the result of the photobiological and the photophysical effects of applying specific wavelengths of light. More specifically, the results and benefits of phototherapy are from the direct effect of the light itself, not from the delivery device such as a laser, an LED light, or other non-laser application methods.

Specifically, various treatments with infrared light are considered beneficial for the treatment of a variety of ailments. Visible reddish light at wavelengths between 630 nm and 660 nm penetrates tissue to a depth of about one third of an inch. This light is very beneficial in treating ailments close to the surface of the skin such as injuries, cuts, scars. This light is particularly effective in treating microbial infections. This light also activates the trigger and acupuncture points of a body and travels through the nervous system of a body, much like that of wires inside electrical conduits. Infrared light, which is still considered to be in the near-infrared spectrum of 700 nm to 1400 nm, penetrates tissues to a depth of about 1.5 inches. At this depth of penetration, the light is highly effective in treating joints, deep muscle, organs and other tissues. Near infrared light focused on the body during moderate exercise has profound effects, through thermal and non-thermal exposure. Localized heat increases tissue temperatures, tissue oxygen partial pressures, and tissue blood flow. These effects cause increased tissue metabolism which mobilizes and burns fats during exercise. Non-thermal effects include long-lasting cellular protective effects involving cell membrane enzymes, neuronal growth, protein ferritin, mitochondria ATP production and others. Such results are observed in only four weeks with near infrared irradiation during moderate bicycle endurance. Additionally, during a single exercise irradiation session, acute positive reactions, such as pain reduction, occur. Immediate changes in blood concentrations enhance physical work load and the physical capacity of participants. The effects of using near infrared during exercise improves body composition, especially local fat distribution, and reduce fat and body weight in obese persons.

The portable near-infrared radiant exercise tent provides people with a means to utilize near infrared light to lose weight, change body composition, and reduce pain during exercise in their own homes. The radiant tent material stops near infrared rays from escaping the enclosure, so they bounce around and bombard the body with additional phototherapy during an exercise or sauna session. Consequently, heat is contained and the need to preheat of the tent enclosure is eliminated, thereby reducing the amount of time needed to sweat during a sauna session. The radiant tent is modular, such that multiple tents attach to together, creating larger areas for exercise and can accommodate additional users. The radiant tent can be oriented into a variety of positions, by utilizing frame tees or couplings, attaching internal (vertical and/or horizontal) partitions to compartmentalize areas for near infrared sauna therapy while sitting, standing or laying down. The convertible nature of this present invention provides users with the health benefits of near-infrared radiation, maximizes the effectiveness of exercise, while doubling as a sauna enclosure that is comfortable, with portable and modular capabilities.

DETAILED DESCRIPTION OF THE INVENTION

All illustrations of the drawings are for the purpose of describing selected versions of the present invention and are not intended to limit the scope of the present invention.

Figure 1:
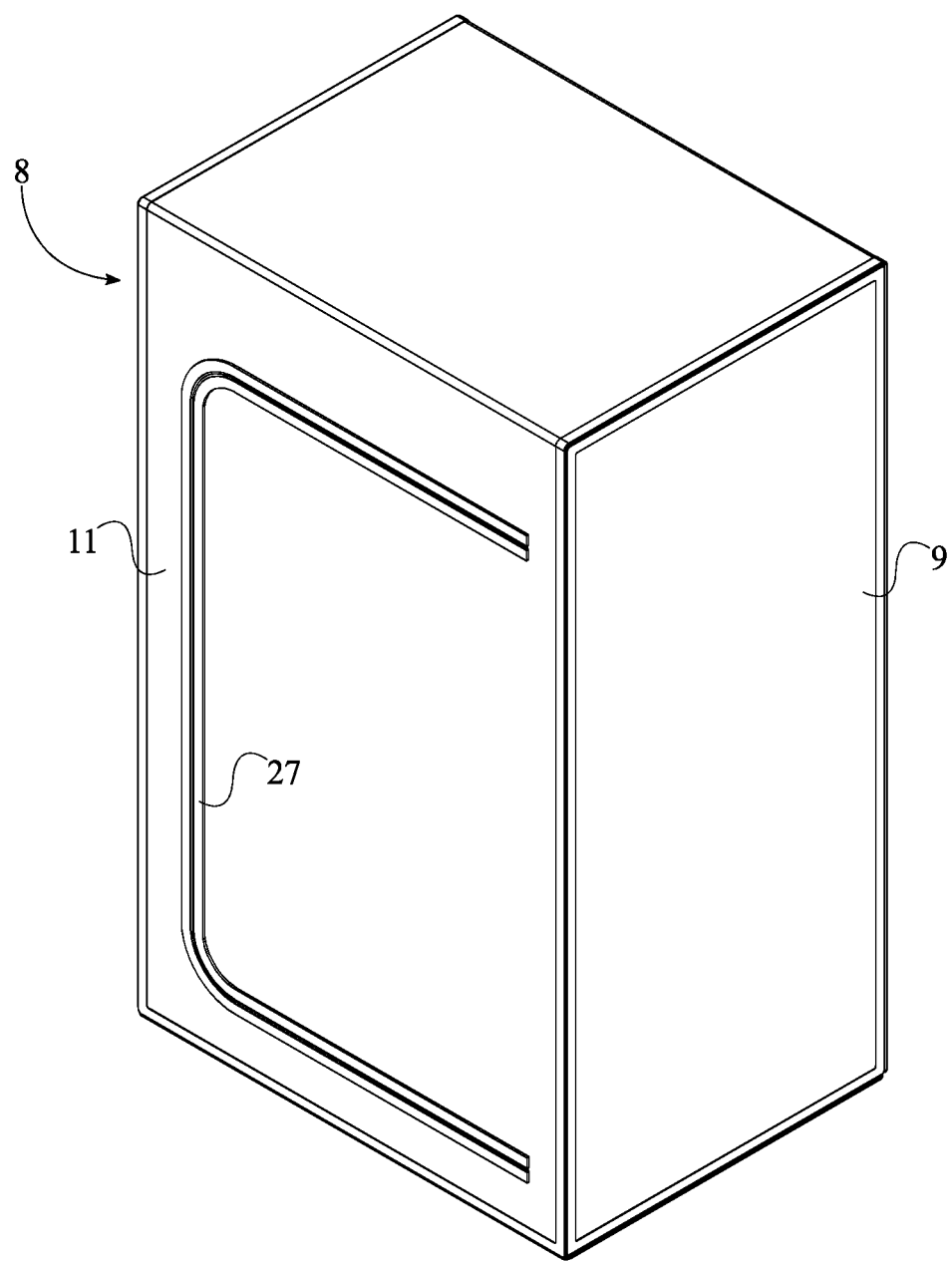
FIG. 1 is a top perspective view of a first embodiment of the present invention that accommodates a single user.
Figure 2:
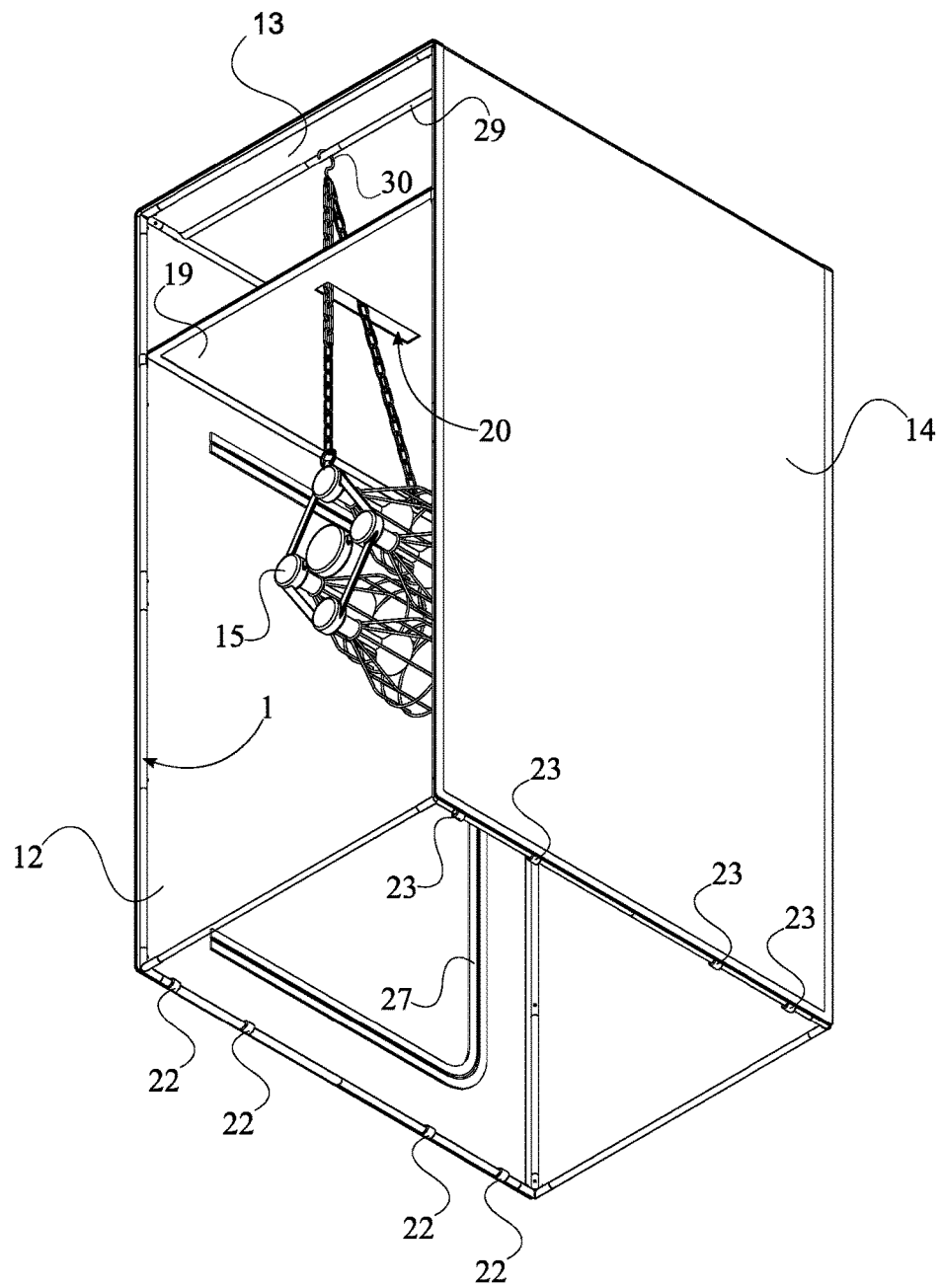
FIG. 2 is a bottom perspective view of the first embodiment of the present invention that accommodates a single user, without the flooring layer and the first panel.

The present invention is a modular portable exercise tent that converts to a sauna tent. The present invention maximizes the amount of heat within an enclosed area using radiant tent panels. The present invention provides phototherapy treatments to a single user or multiple users simultaneously. The present invention changes body composition, increases fat loss, reduces pain, increases cellular energy production (ATP), increases circulation more than traditional saunas through blood shunting, improves condition of skin, blood, arteries, veins, and breast tissue; penetrates deeper into the body and activates trigger and acupuncture points throughout the body of a user. As seen in FIG. 1 and FIG. 2, the present invention comprises a scaffolding 1, a thermally insulative cover 8, and at least one heating lamp 15. The scaffolding 1 upholds the thermally insulative cover 8 and defines the area of heat around a user. The structure of the scaffolding 1 is adjustable so that a user may stand, sit, or lay down within the defined area of the scaffolding 1. The extension and the reduction of the overall size of the scaffolding 1 accommodates the activity of the user within the scaffolding 1. More specifically, the extension in size of the scaffolding 1 allows the user to freely exercise within the scaffolding 1 while being exposed to infrared light. The reduction in size of the scaffolding 1 effectively surrounds the user as he or she rests while being exposed to infrared light, similar to that of a sauna treatment. The thermally insulative cover 8 surrounds the scaffolding 1 and insulates the heat emitted from the at least one heating lamp 15. The thermally insulative cover 8 is preferably made of radiant material as to enhance the phototherapy treatment of the at least one heating lamp 15. The at least one heating lamp 15 provides infrared light within the defined area. In order for the thermally insulative cover 8 to accommodate the modular construction of the scaffolding 1, the thermally insulative cover 8 comprises a first panel 9, a second panel 10, and an overlay panel 11. The overlay panel 11 further comprises a first planar portion 12, a second planar portion 13, and a third planar portion 14 in order to accommodate the structure of the scaffolding 1.

Figure 3:
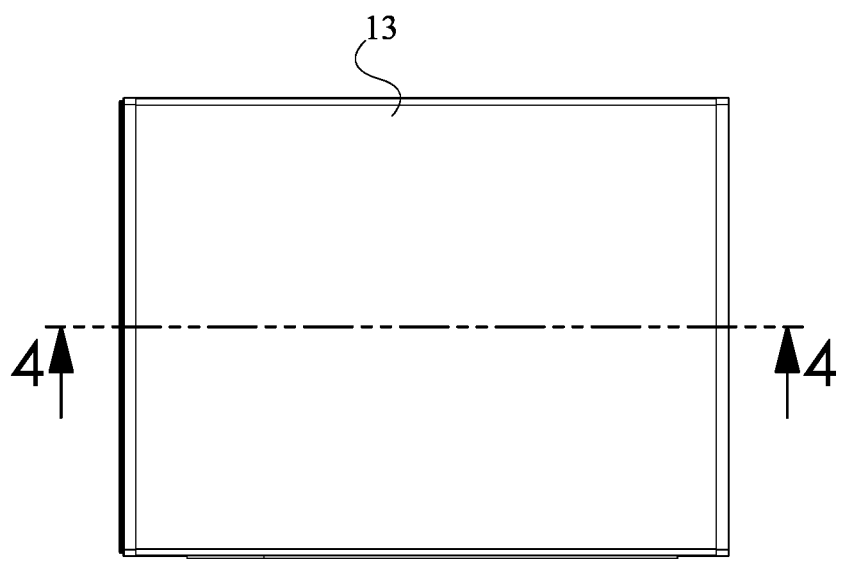
FIG. 3 is a top side view of the first embodiment of the present invention that accommodates a single user.
Figure 4:
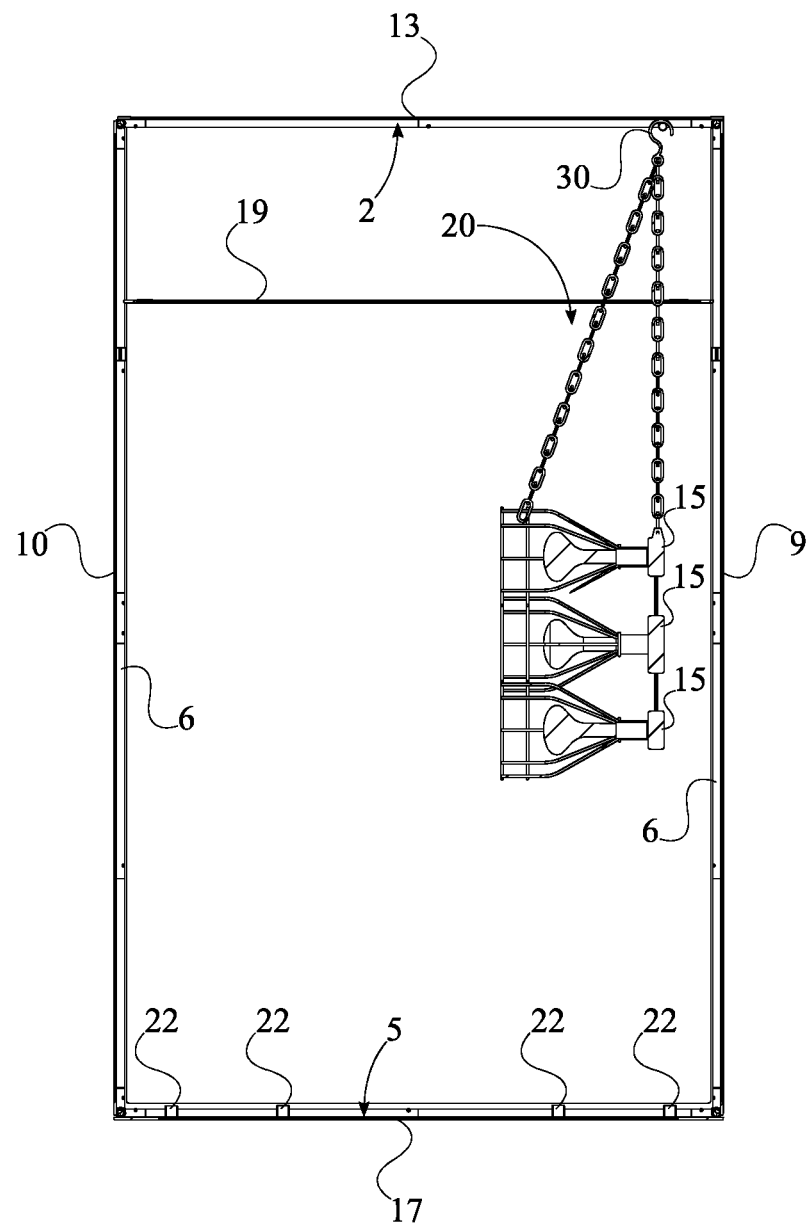
FIG. 4 is a cross-sectional view of FIG. 3, wherein the at least one heating lamp is suspended from the at least one suspension rod.
Figure 7:
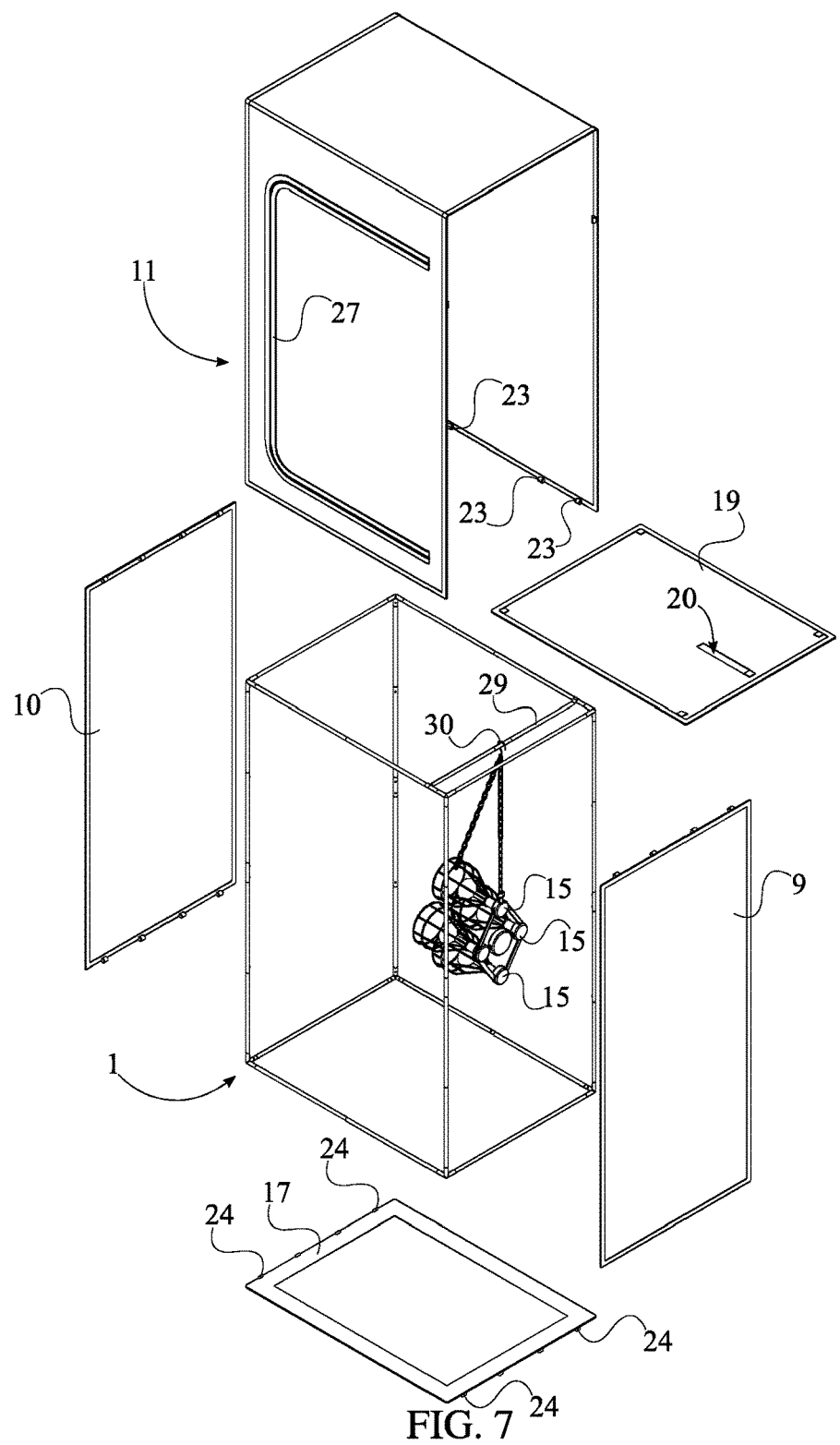
FIG. 7 is an exploded view of the first embodiment of the present invention that accommodates a single user.
Figure 8:
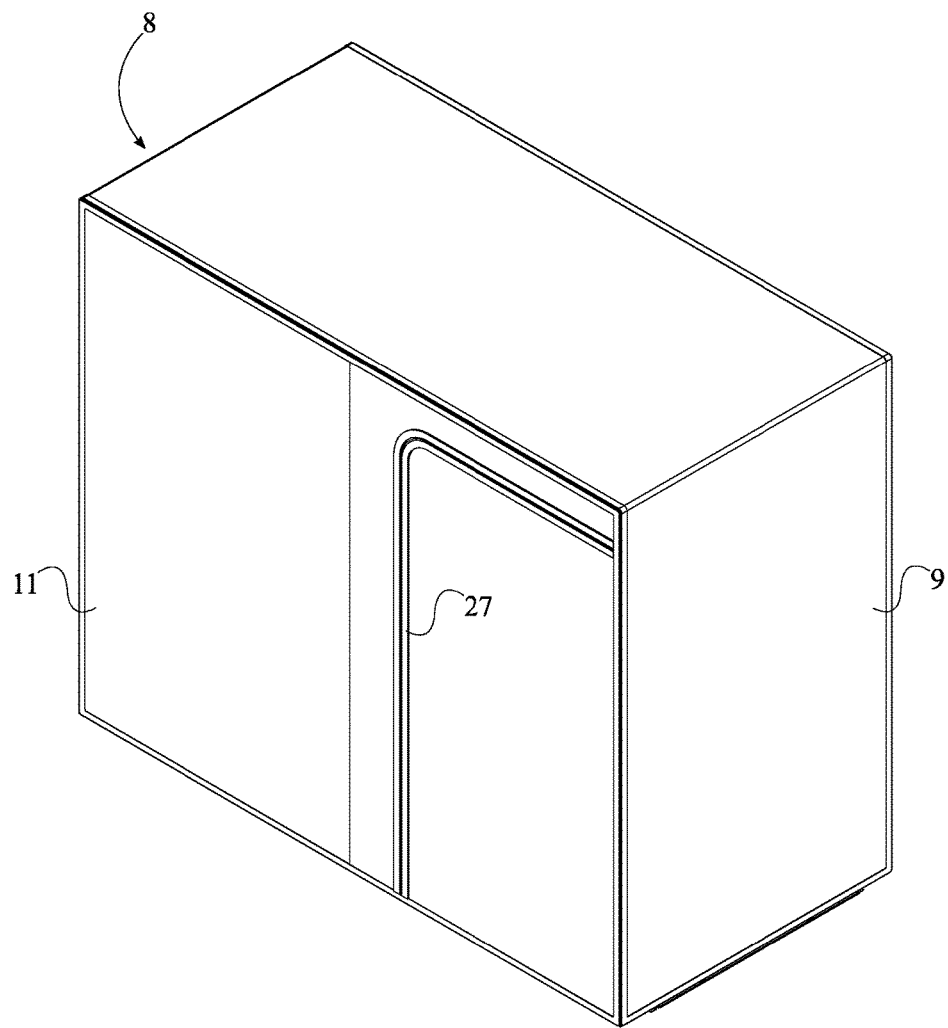
FIG. 8 is a top perspective view of a second embodiment of the present invention that accommodates at least one user.
Figure 9:
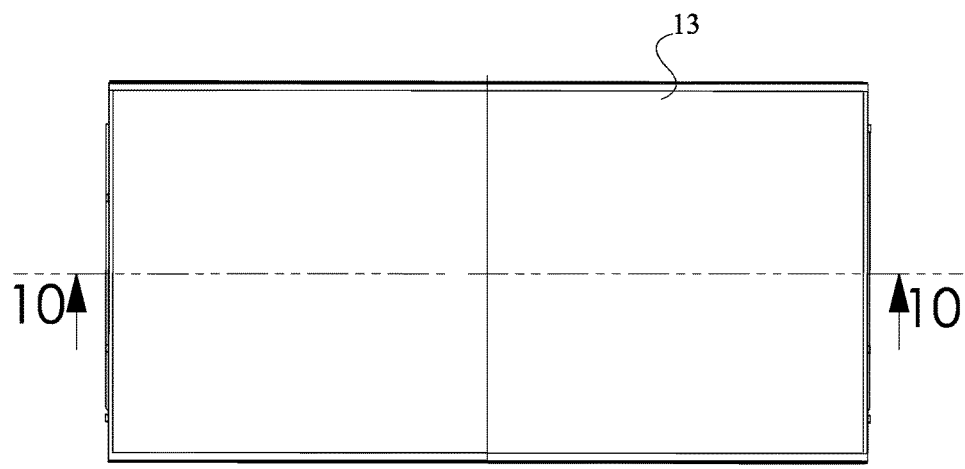
FIG. 9 is a top side view of the second embodiment of the present invention that accommodates at least one user.

The configuration of the aforementioned components facilitates the infrared light treatment of a user while exercising, standing, sitting, or laying down. In order to prevent the heat emitted from the at least one heating lamp 15 from escaping past the scaffolding 1, the thermally insulative cover 8 is tensionably mounted over the scaffolding 1, as illustrated in FIG. 2, FIG. 3, and FIG. 4. More specifically, the first panel 9 is positioned adjacent to the overlay panel 11, and the second panel 10 is positioned adjacent to the overlay panel 11, opposite to the first panel 9, shown in FIG. 1 and FIG. 7. The first panel 9 and the second panel 10 are positioned parallel to each other. The overlay panel 11 is attached adjacent to the scaffolding 1 in between the first panel 9 and the second panel 10, conforming to the structure of the scaffolding 1. This configuration encloses the thermally insulative cover 8 around the scaffolding 1. Moreover, the overlay panel 11 is positioned perpendicular to the first panel 9 and the second panel 10. The first planar portion 12 is hingedly connected to the second planar portion 13. Similarly, the third planar portion 14 is hingedly connected to the second planar portion 13, positioned opposite to the first planar portion 12, thereby facilitating the assembly of the thermally insulative cover 8 about the scaffolding 1. In the preferred embodiment of the present invention, the first planar portion 12 and the third planar portion 14 are positioned perpendicular to the second planar portion 13. The at least one heating lamp 15 is mounted within the scaffolding 1, as to contain the heat within the thermally insulative cover 8. The at least one heating lamp 15 is preferably suspended within the thermally insulative cover 8, as seen in FIG. 2 and FIG. 4.

Figure 5:
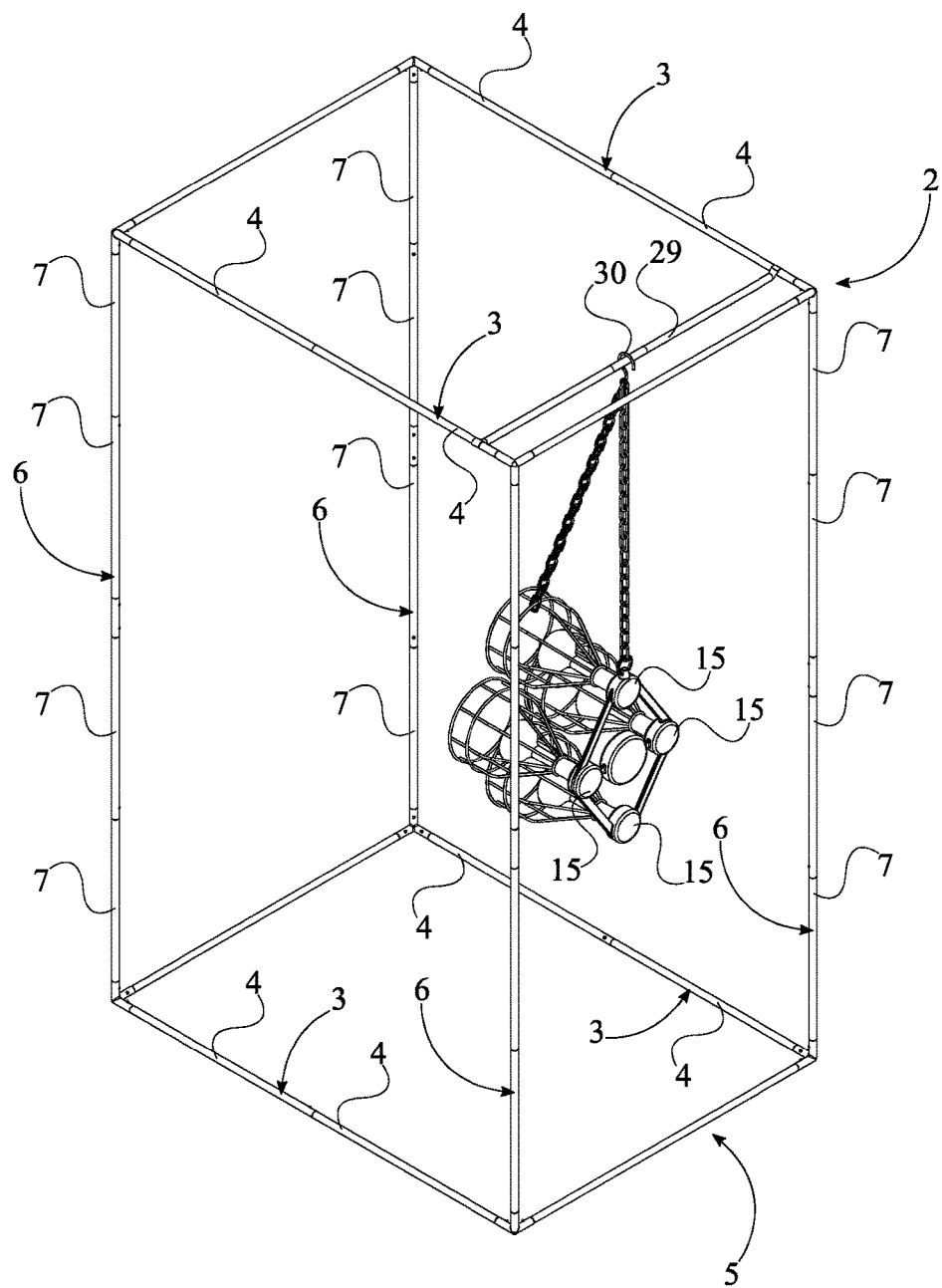
FIG. 5 is a top perspective view of the scaffolding and at least one heating lamp of the first embodiment of the present invention that accommodates a single user wherein the at least one heating lamp is suspended from the at least one suspension rod.
Figure 6:
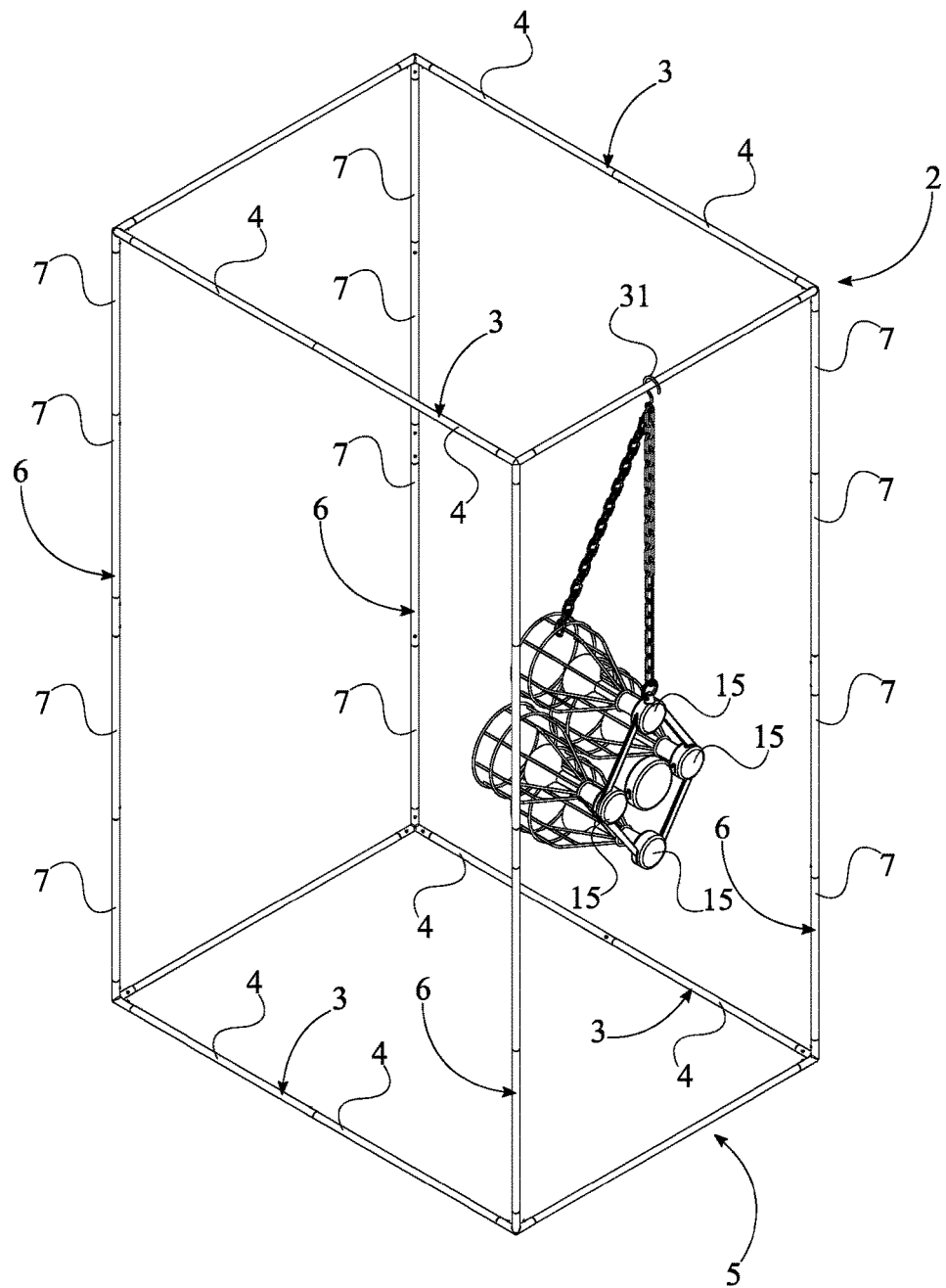
FIG. 6 is a top perspective view of the scaffolding and at least one heating lamp of the first embodiment of the present invention that accommodates a single user wherein the at least one heating lamp is suspended from the scaffolding.

In order for the structure of the scaffolding 1 to be adjustable according to the position of the user within the present invention, the scaffolding 1 comprises a first base frame 2, a second base frame 5, and a plurality of lateral posts 6, illustrated in FIG. 5 and FIG. 6. The plurality of lateral posts 6 defines the distance from the first base frame 2 to the second base frame 5 and accommodates the position of the user within the scaffolding 1. The first base frame 2 and the second base frame 5 allows the plurality of lateral posts 6 to surround the user. The first base frame 2 is terminally connected to each of the plurality of lateral posts 6. Similarly, the second base frame 5 is terminally connected to each of the plurality of lateral posts 6, opposite the second base frame 5. More specifically, the plurality of lateral posts 6 is positioned normal to both the first base frame 2 and the second base frame 5 and is laterally distributed around the scaffolding 1. This configuration allows the scaffolding 1 to accommodate a user that is standing, sitting or lying down within the scaffolding 1.

In the preferred embodiment of the present invention, the first base frame 2 comprises a plurality base posts 3, seen in FIG. 5 and FIG. 6. The plurality of base posts 3 defines the overall structure of the first base frame 2. The plurality of base posts 3 is arranged into an overall polygonal shape in order to support the plurality of lateral posts 6 and the thermally insulative cover 8. The overall polygonal shape of the first base frame 2 is preferably a square, which accommodates a single user. In order to accommodate two or more users, the first base frame 2 is rectangular. This rectangular configuration allows at least one user to freely exercise within the scaffolding 1. More specifically, each of the plurality of base posts 3 is terminally connected to a corresponding vertex of the overall polygonal shape. Similarly, the second base frame 5 comprises a plurality of base posts 3, which defines the overall structure of the second base frame 5. The plurality of base posts 3 is arranged into an overall polygonal shape in order to support the plurality of lateral posts 6 and the thermally insulative cover 8. The overall polygonal shape preferably mirrors the overall polygonal shape of the first base frame 2 which is a square. More specifically, each of the plurality of base posts 3 is terminally connected to a corresponding vertex of the overall polygonal shape.

Furthermore, in the preferred embodiment of the present invention, each of the plurality of lateral posts 6 comprises a plurality of assembly rods 7, illustrated in FIG. 5 and FIG. 6. The plurality of assembly rods 7 allows the area within the scaffolding 1 to shrink and expand depending on the position of the user within the scaffolding 1. More specifically, the height of the scaffolding 1 may be adjusted with the addition or removal of one or more of the plurality of assembly rods 7. The extension in height of the scaffolding 1 may accommodate the user while he or she is exercising or standing while receiving the infrared light treatment. The reduction in height of the scaffolding 1 allows thermally insulative cover 8 to effectively surround the user while he or she is sitting down or laying down while receiving infrared light treatment. The plurality of assembly rods 7 is serially attached to each other, thereby preserving the overall shapes of the first base frame 2 and the second base frame 5 while shrinking or expanding the size of the scaffolding 1. Similarly, the both the first base frame 2 and the second base frame 5 comprises a plurality of base posts 3, each of which comprise a plurality of assembly rods 4. The plurality of base posts 3 is arranged into an overall polygonal shape, effectively supporting the plurality of lateral posts 6 and defining the shape of the first base frame 2 and the second base frame 5, respectively. The plurality of assembly rods 4 of both the first base frame 2 and the second base frame 5 however adjust both the size and the overall shape of the scaffolding 1. In order for each of the base posts shrink or expand in length, the plurality of assembly rods 4 is serially attached to each other, similar to that of the plurality of lateral posts 6. In the preferred embodiment of the present invention, the first panel 9, the second panel 10, the first planar portion 12, and the third planar portion 14 are positioned around the plurality of lateral posts 6. This configuration prevents any heat from escaping the defined area of the scaffolding 1. More specifically, the third planar portion 14 is positioned adjacent the first base frame 2.

Figure 12:
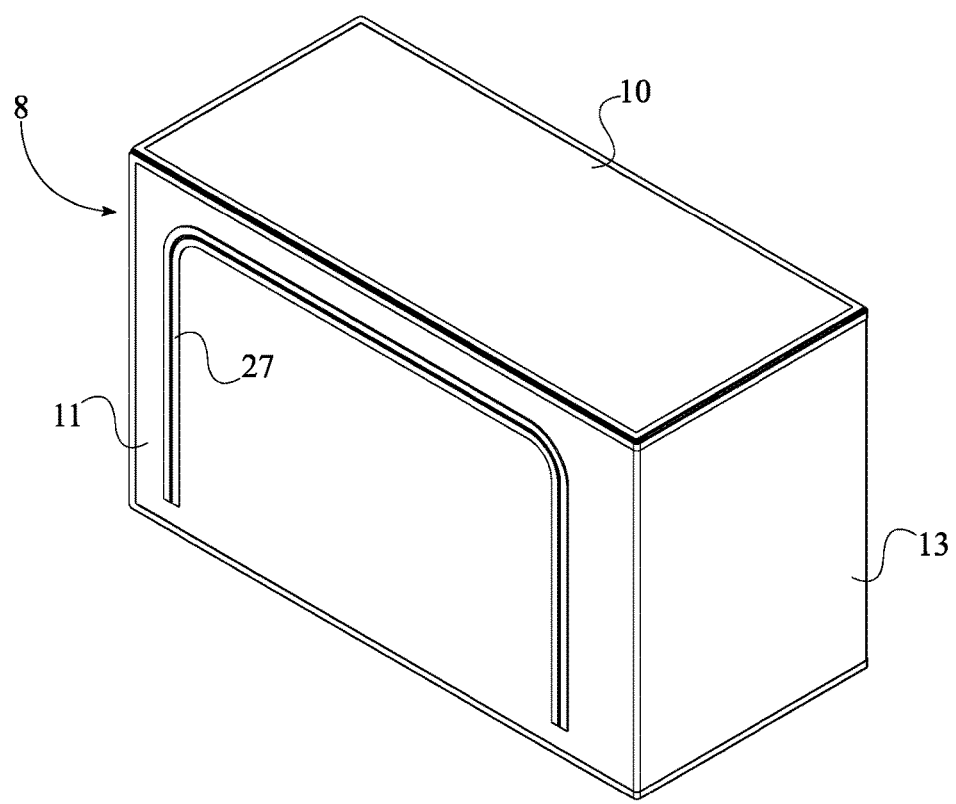
FIG. 12 is a top perspective view of a first embodiment of the present invention in a horizontal orientation.
Figure 13:
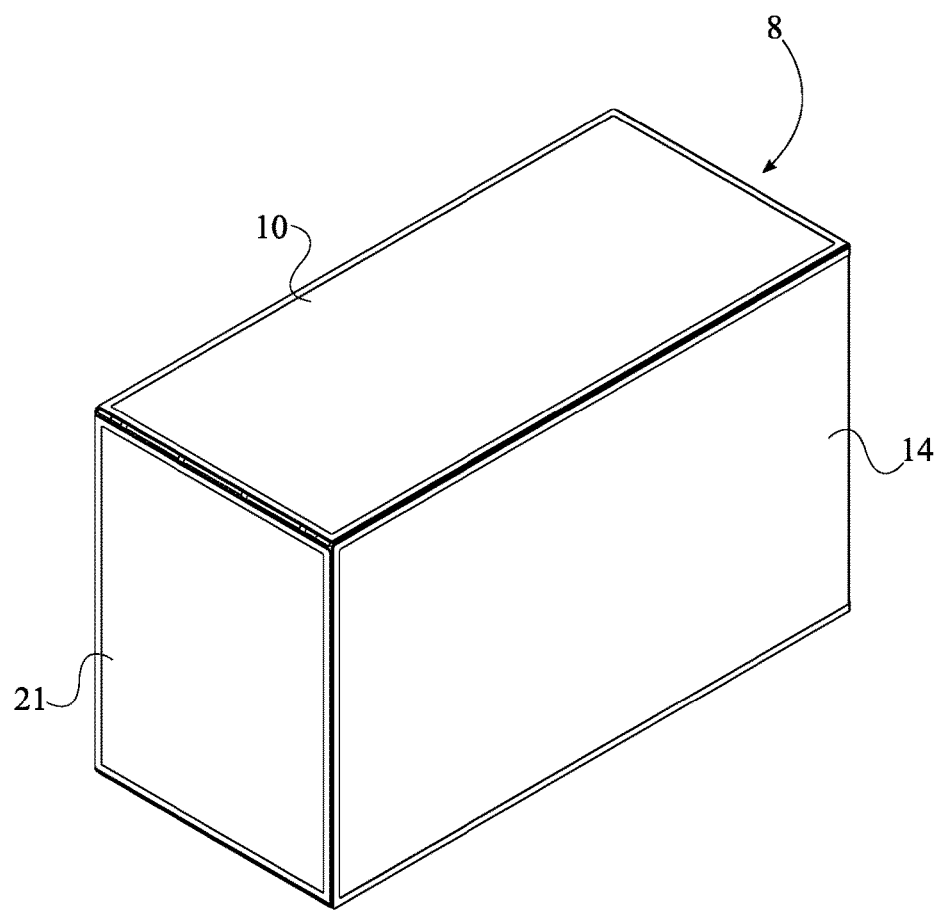
FIG. 13 is a rear perspective view of a first embodiment of the present invention in a horizontal orientation.
Figure 14:
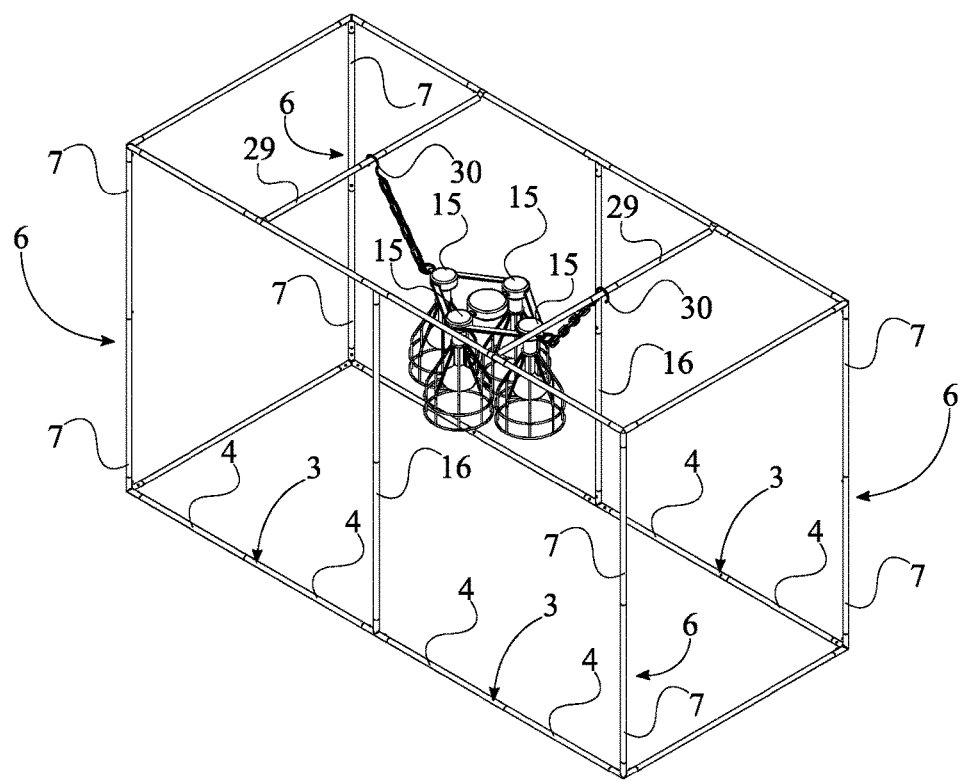
FIG. 14 is a top perspective view of the scaffolding and at least one heating lamp of the first embodiment of the present invention in a horizontal orientation.

The present invention further comprises at least one support post 16, seen in FIG. 14. The at least one support post 16 reinforces the position of adjacent lateral posts of the plurality of lateral posts 6. More specifically, the scaffolding 1 is oriented in a horizontal configuration such that the length of the scaffolding 1 is extended, as shown in FIG. 8, FIG. 9, FIG. 10, and FIG. 11. Alternatively, the plurality of lateral posts 6 is adjacent the ground and both the first base frame 2 and the second base frame 5 are oriented perpendicular to the ground, as shown in FIG. 12, FIG. 13, and FIG. 14. This horizontal orientation reduces the defined area of the scaffolding in order to accommodate a user laying down within the scaffolding 1. In order to accommodate a single user sitting or lying down within the scaffolding 1, the scaffolding 1 is tilted to the side so that the overlay panel 11 attached to the scaffolding 1 while in the vertical orientation may remain attached to the scaffolding 1 while in the horizontal configuration. The at least one support post 16 is connected in between an arbitrary lateral post and an adjacent lateral post, wherein the arbitrary lateral post and the adjacent lateral post are from the plurality of lateral posts 6. This connection supports the weight of the at least one heating lamp 15 that is suspended from the scaffolding 1. Moreover, the at least one support post 16 is positioned perpendicular to the arbitrary lateral post and the adjacent lateral post. In order to accommodate at least one user, the length of the scaffolding 1 is extended by extending the first base frame 2 and the second base frame 5. Additional lateral posts of the plurality of lateral posts 6 may be integrated into the scaffolding 1 in order to support the at least one heating lamp 15.

In the preferred embodiment further comprises at least one flooring layer 17, as seen in FIG. 4, FIG. 7, FIG. 10, and FIG. 11. The at least one flooring layer 17 provides a comfortable and protective surface for which a user may step upon or lay down on while surrounded by the scaffolding 1 and the thermally insulative cover 8. The at least one flooring layer 17 is preferably flexible such that the at least one flooring layer 17 may be rolled or folded by the user. The at least one flooring layer 17 is mounted adjacent the scaffolding 1 and is positioned external to the thermally insulative cover 8. This configuration accommodates the modular structure of the scaffolding 1 and the convertible size of the thermally insulative cover 8. In order to further accommodate the modular structure of the scaffolding 1, the present invention further comprises a plurality of third fasteners 24. The plurality of third fasteners 24 is perimetrically distributed across the flooring layer. An arbitrary flooring layer of the at least one flooring layer 17 is connected to an adjacent flooring layer of the at least one flooring layer 17 by the plurality of third fasteners 24 so that the user does not accidentally come into contact with the surface beneath both the arbitrary flooring layer and the adjacent flooring layer of the at least one flooring layer 17. Moreover, this configuration effectively encloses defined area of the scaffolding. This configuration best accommodates the scaffolding 1 in a horizontal configuration. In order to prevent the at least one flooring layer 17 from moving about the scaffolding 1, the plurality of third fasteners 24 connect the flooring layer to the scaffolding 1. The at least one flooring layer 17 is preferably made of a bamboo material with a radiant thermal backing. The bamboo material further enhances the relaxing environment within thermally insulative cover 8.

Figure 22:
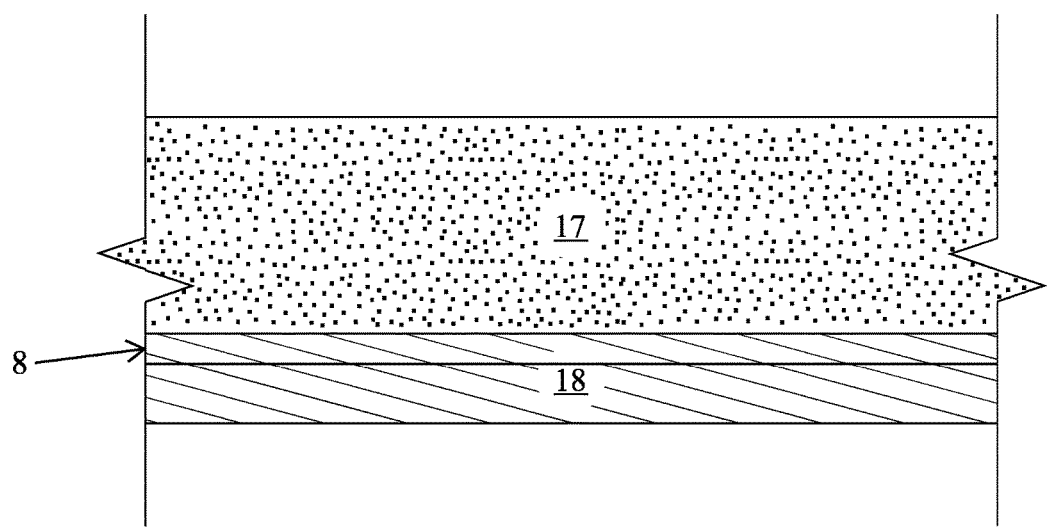
FIG. 22 is a schematic view of the at least one flooring layer and the thermal backing layer.

The preferred embodiment of the present invention further comprises a thermal backing layer 18, illustrated in FIG. 22. The thermal backing layer 18 provides more insulation to the enclosed area within the thermal insulative cover. In order to prevent heat from escaping past the at least one flooring layer 17, the thermal backing layer 18 is superimposed across the at least one flooring layer 17. The user does not come into contact or rest on the thermal backing layer 18 as the thermal backing layer 18 is positioned external to the thermally insulative cover 8. The thermal backing layer 18 does not inhibit the comfort and presentation of the at least one flooring layer 17.

Figure 10:
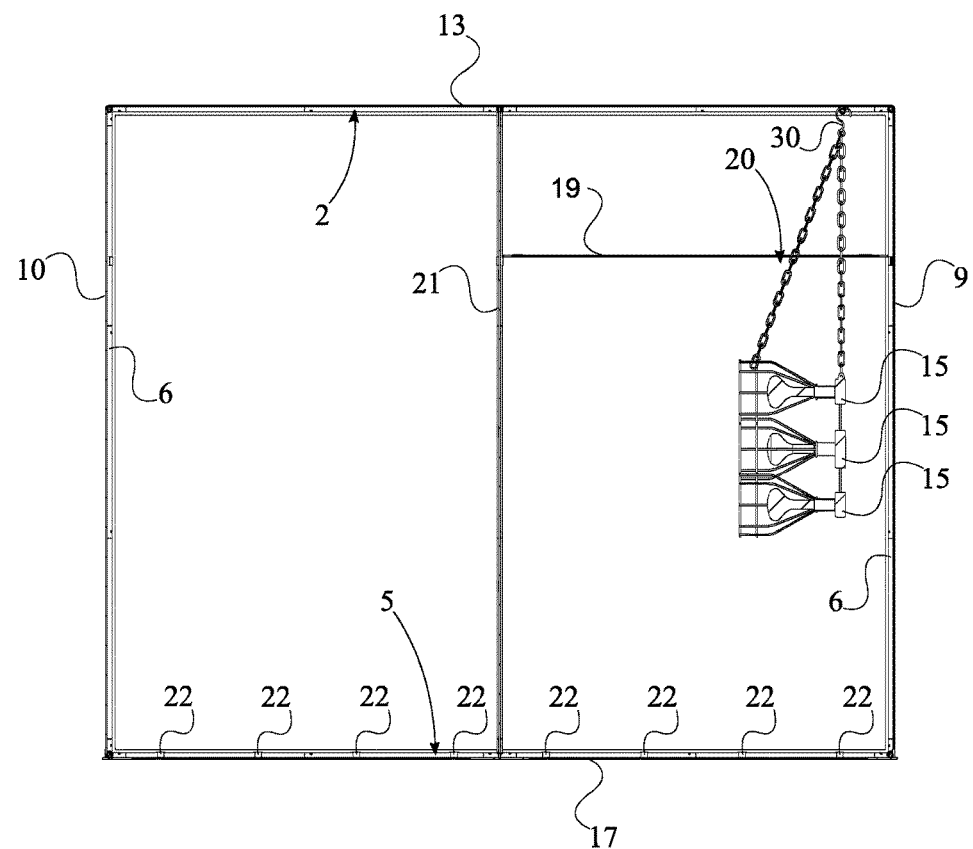
FIG. 10 is a cross-sectional view of FIG. 9, wherein the first supplementary thermal insulative panel and the second supplementary thermal insulative panel are attached to the scaffolding.
Figure 11:
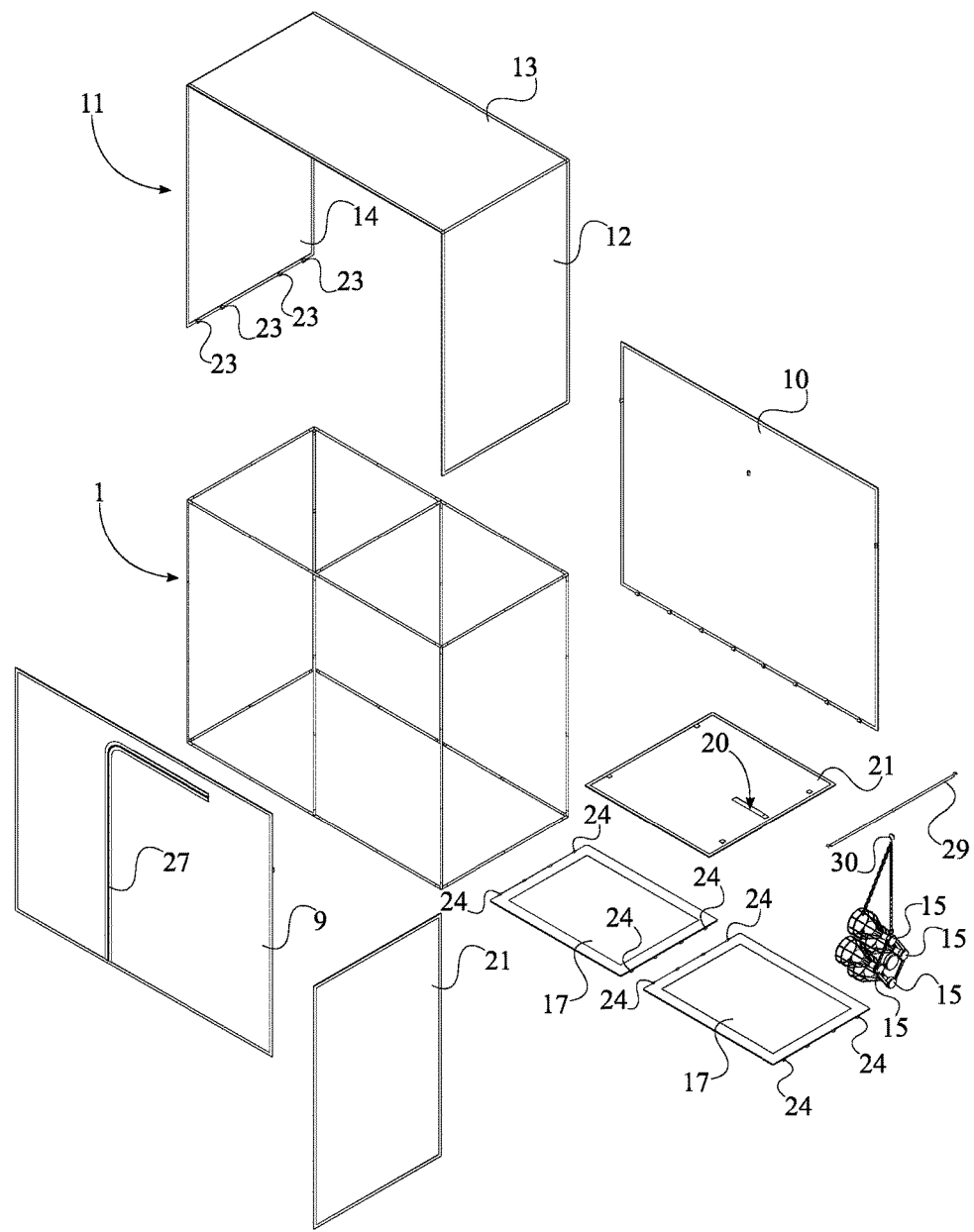
FIG. 11 is an exploded view of the second embodiment of the present invention that accommodates at least one user.

In order to divide the area within the thermally insulative cover 8 or shrink the area within the thermally insulative cover 8, the present invention further comprises a at least one first supplementary thermal insulative panel 19 and a second supplementary thermal insulative panel 21, illustrated in FIG. 10, FIG. 11, and FIG. 13. As shown in FIG. 10, the at least one first supplementary thermal insulative panel 19 divides the enclosed area within the thermally insulative cover 8. As shown in FIG. 13, the second supplementary thermal insulative panel 21 seals an opening of the thermally insulative cover 8 when the scaffolding 1 is in a horizontal orientation. Both the first supplementary thermal insulative panel 19 and the second supplementary thermal insulative panel 21 are preferably secured to the scaffolding 1 with a set of hook and loop fasteners. It is understood that a variety of fasteners may secure the first supplementary thermal insulative panel 19 and the second supplementary thermal insulative panel 21 to the scaffolding 1. The at least one first supplementary thermal insulative panel 19 is mounted adjacent within the scaffolding 1. The at least one first supplementary thermal insulative panel 19 may be oriented horizontally or vertically within the scaffolding 1. An alternate embodiment of the present invention comprises a slot 20 which accommodates the suspension of the at least one heating lamp 15. The slot 20 traverses into the at least one first supplementary thermal insulative panel 19. The second supplementary thermal insulative panel 21 is mounted adjacent to the scaffolding 1 and is positioned external to the thermally insulative cover 8. The second supplementary thermal insulative panel 21 is preferably secured to the scaffolding 1 with the scaffolding 1 in a horizontal configuration. More specifically, while in the horizontal configuration, the first panel 9 is removed from the scaffolding 1 and replaced with at least one flooring layer 17. The second supplementary panel is adjacent to the overlay panel 11, positioned opposite the second planar portion 13, thereby enclosing the area within the scaffolding 1.

Figure 15:
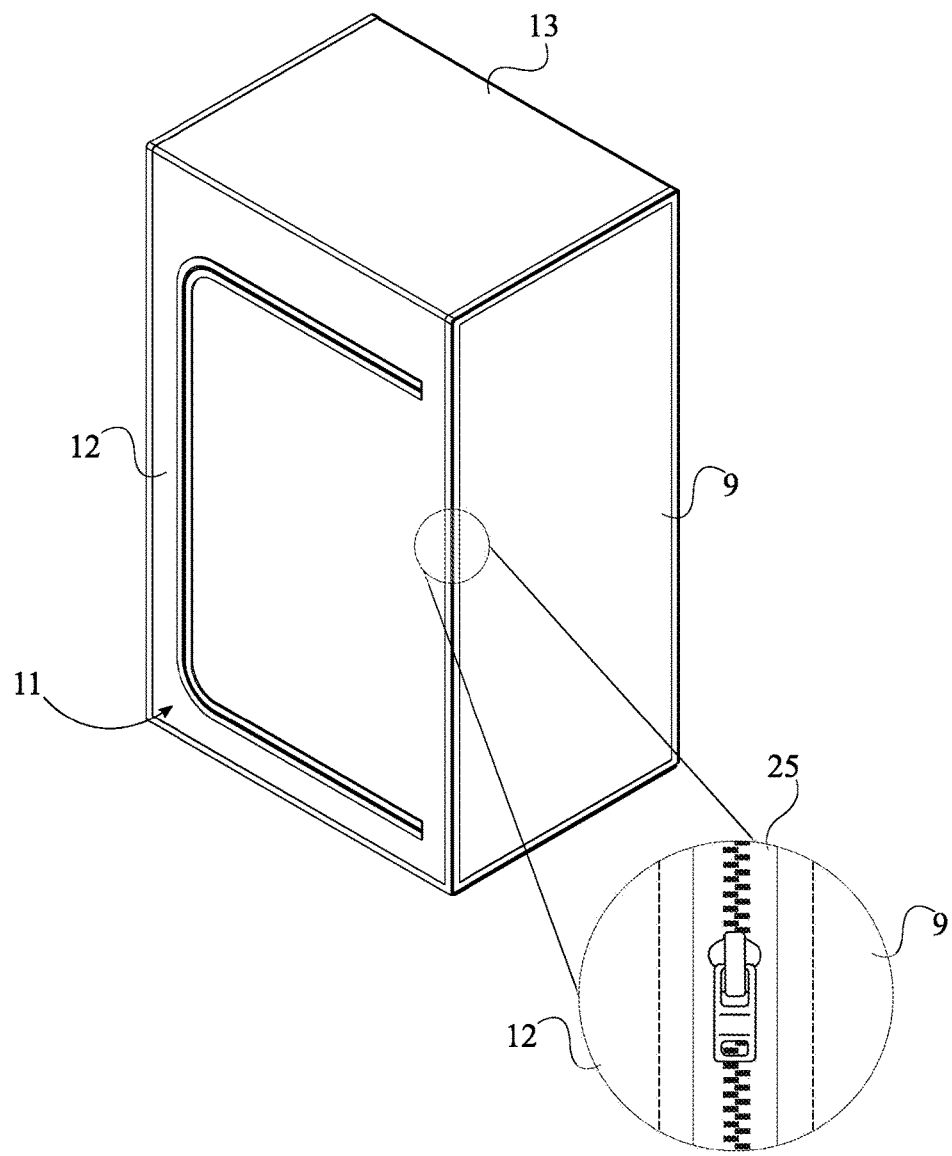
FIG. 15 is a magnified view of the first binding of the first embodiment of the present invention that accommodates a single user.
Figure 16:
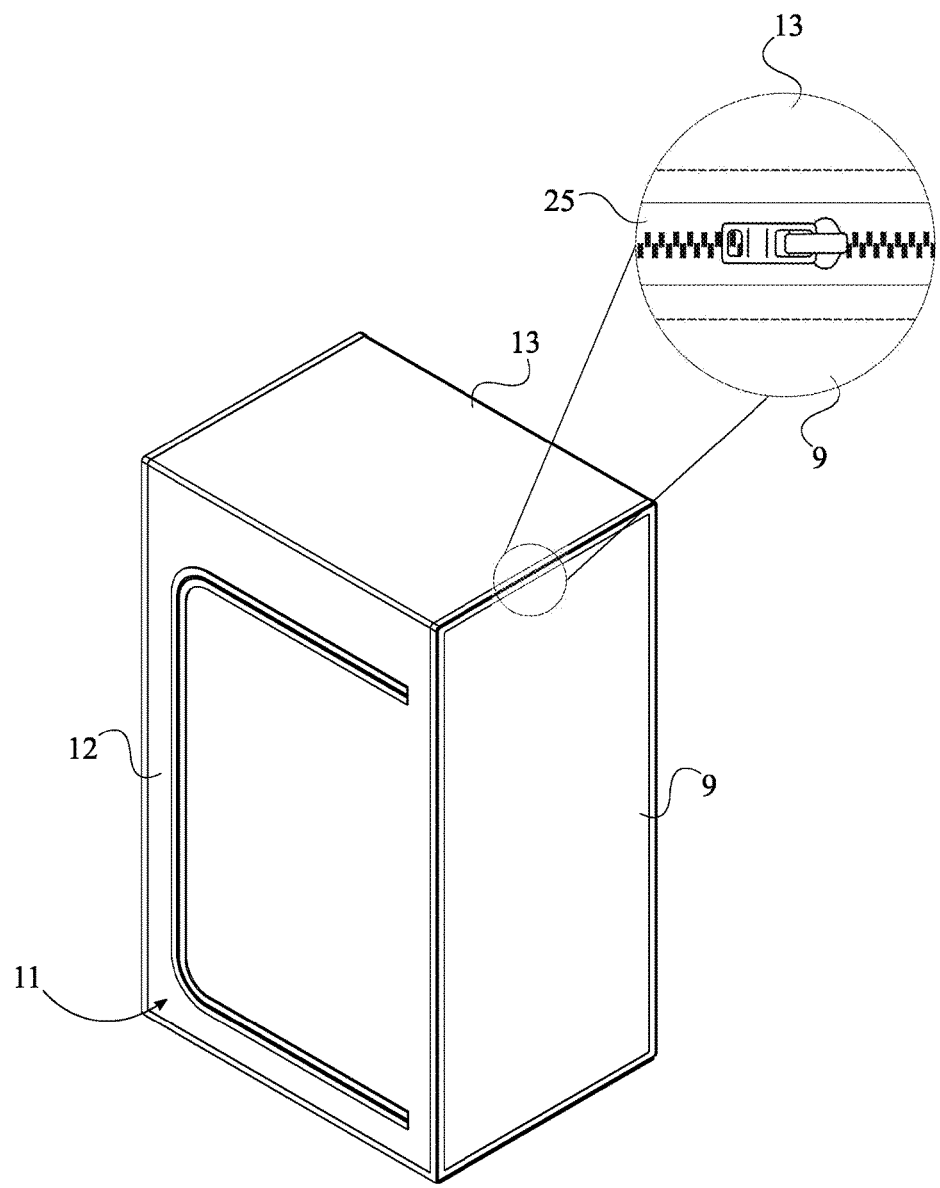
FIG. 16 is a magnified view of the first binding of the first embodiment of the present invention that accommodates a single user.
Figure 17:
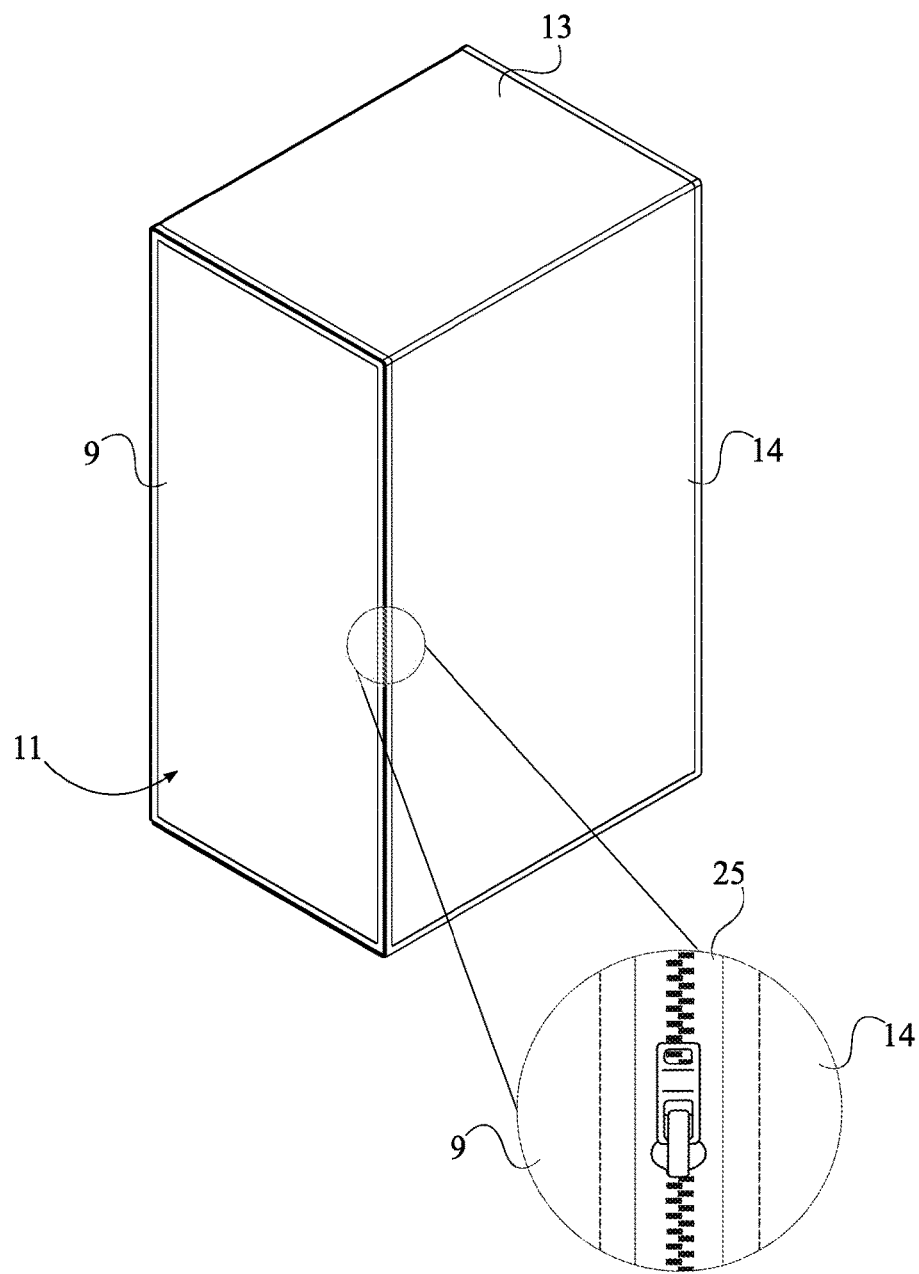
FIG. 17 is a magnified view of the first binding of the first embodiment of the present invention that accommodates a single user.
Figure 18:
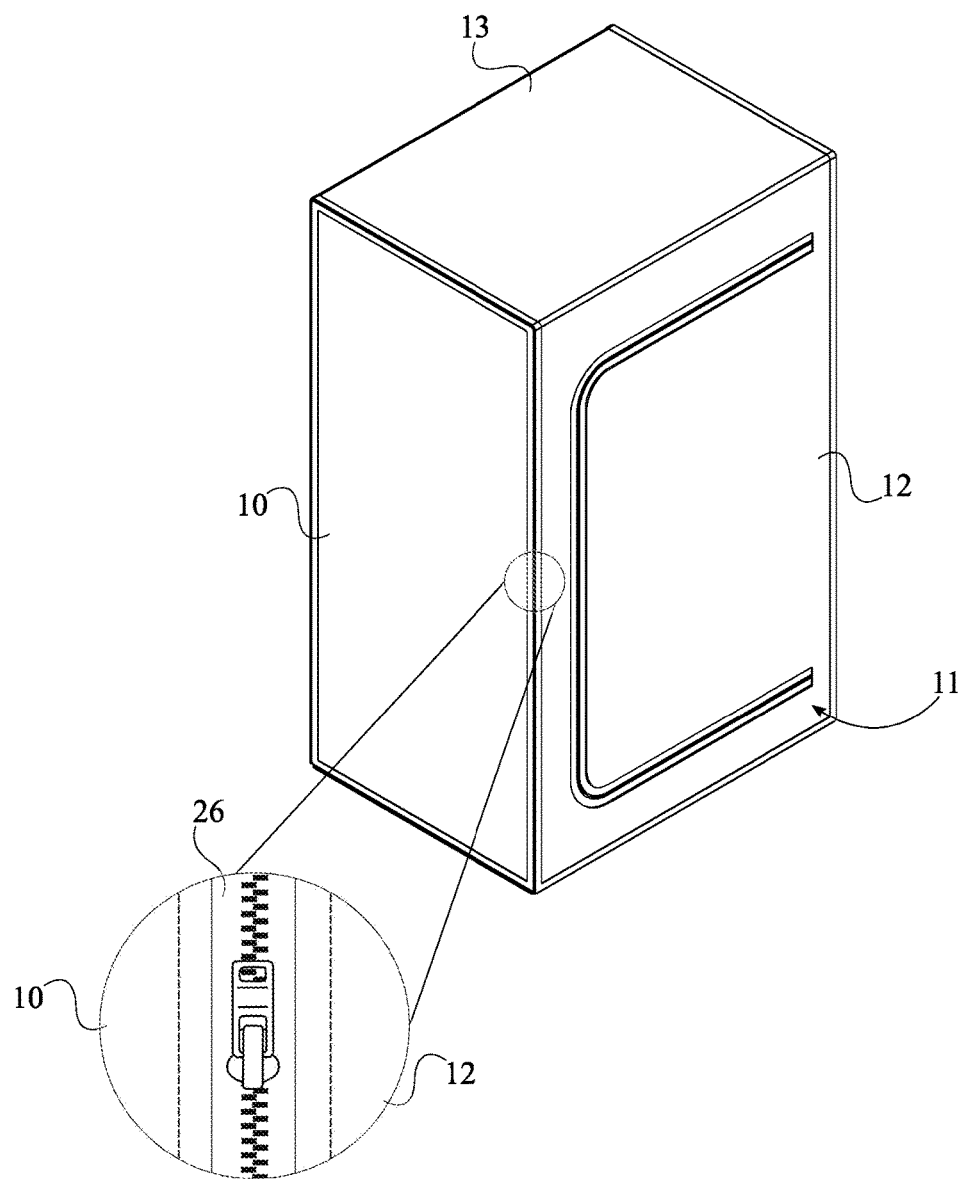
FIG. 18 is a magnified view of the second binding of the first embodiment of the present invention that accommodates a single user.
Figure 19:
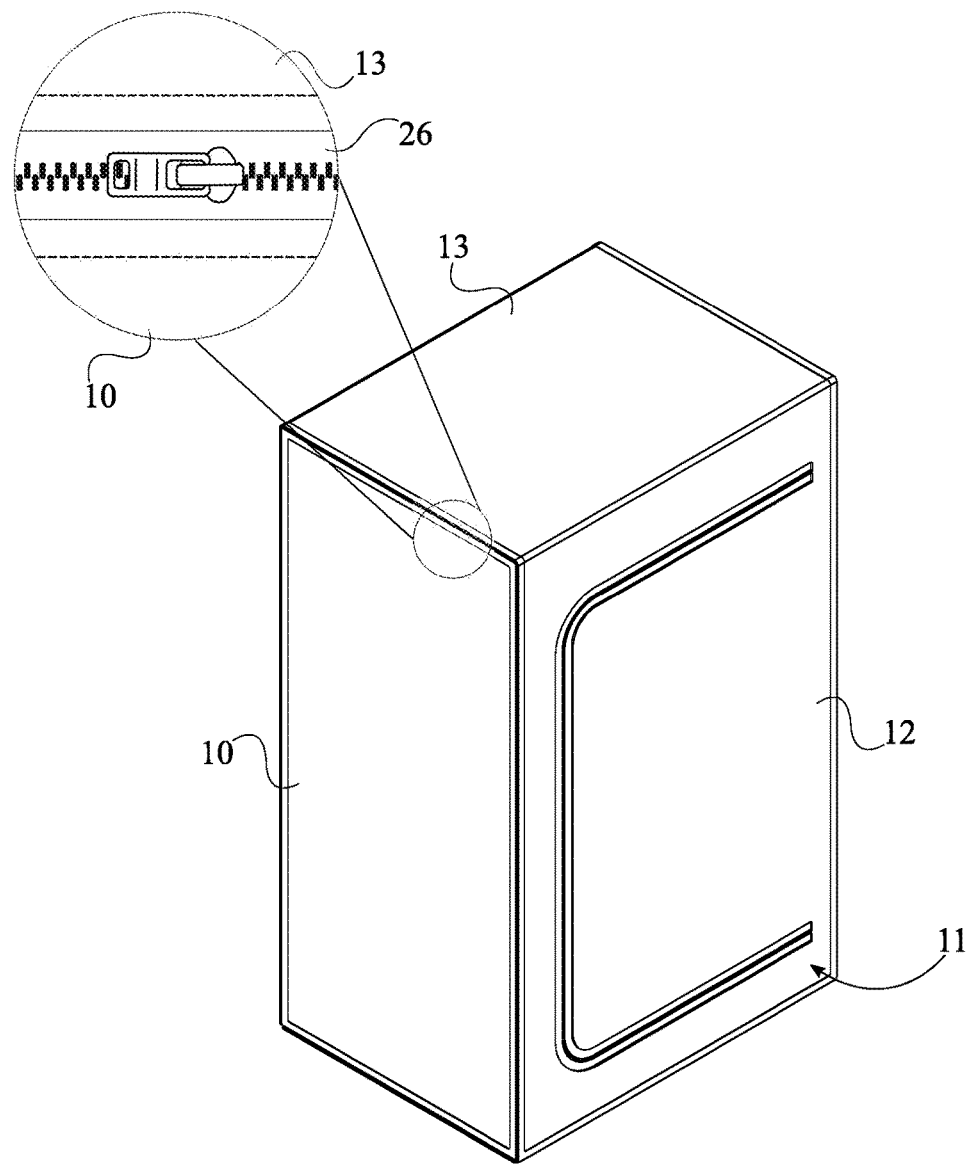
FIG. 19 is a magnified view of the second binding of the first embodiment of the present invention that accommodates a single user.
Figure 20:
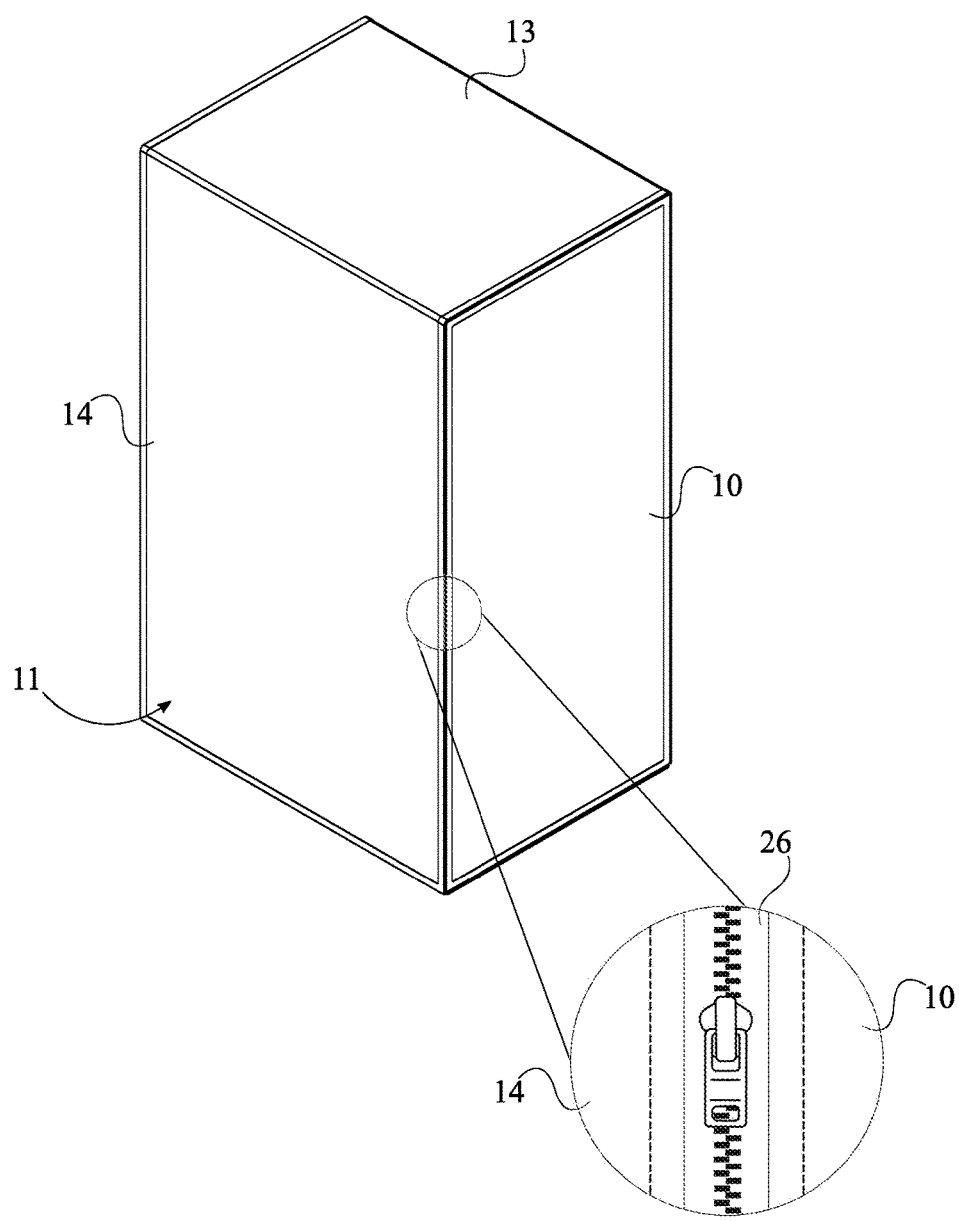
FIG. 20 is a magnified view of the second binding of the first embodiment of the present invention that accommodates a single user.

The preferred embodiment of the present invention further comprises a plurality of first fasteners 22 and a plurality of second fasteners 23, shown in FIG. 2, FIG. 4, FIG. 7, FIG. 10, and FIG. 11. The plurality of first fasteners 22 and the plurality of second fasteners 23 each secure the thermally insulative cover 8 to the scaffolding 1. More specifically, the first planar portion 12 is peripherally attached to the scaffolding 1 by the plurality of first fasteners 22, and the third planar portion 14 is peripherally attached to the scaffolding 1 by the plurality of second fasteners 23. In order to secure the first panel 9 and the second panel 10 to the overlay panel 11, the present invention further comprises a first binding 25 and a second binding 26. The first planar portion 12, the second planar portion 13, and the third planar portion 14 are peripherally attached to the first panel 9 by the first binding 25, as seen in FIG. 15, FIG. 16, and FIG. 17. The first planar portion 12, the second planar portion 13, and the third planar portion 14 are peripherally attached to the second panel 10 by the second binding 26, as seen in FIG. 18, FIG. 19, and FIG. 20. This configuration allows thermally insulative cover 8 to surround the scaffolding 1 regardless of the overall structure of the scaffolding 1.

Figure 21:
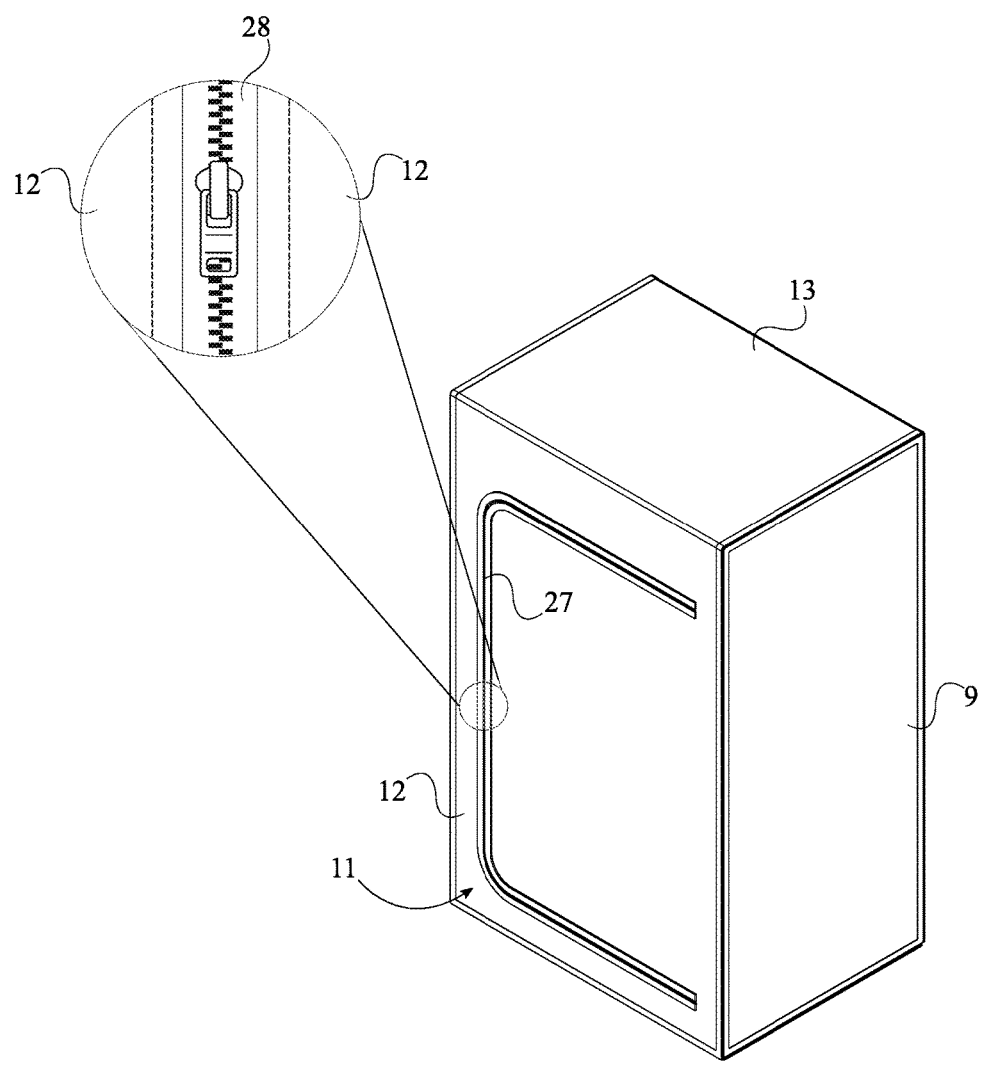
FIG. 21 is a magnified view of the third binding of the first embodiment of the present invention that accommodates a single user.

In order for a user to enter the defined area of the scaffolding 1, within the thermally insulative cover 8, the present invention comprises a door-defining slit 27, seen in FIG. 1, FIG. 7, FIG. 8, FIG. 11, and FIG. 12. The door-defining slit 27 preferably traverses through the first panel 9. However, it is understood in alternate embodiments of the present invention, the door-defining slit 27 may traverse through the second panel 10, the first planar portion 12 of the overlay panel 11, or the third planar portion 14 of the overlay panel 11. In order to seal the door-defining slit 27, the present invention comprises a third binding 28. As seen in FIG. 21, the third binding 28 is operatively integrated into the door-defining slit 27, wherein the third binding 28 is used to open and close the door-defining slit 27. The third binding 28 is preferably a zipper that allows a user to easily open and close the door-defining slit 27, the third binding 28 may be a variety of fasteners that effectively seals the door-defining slit 27.

The configuration of the scaffolding 1 and the thermally insulative cover 8, as described, allows the at least one heating lamp 15 to effectively provide heat within the area that is both defined by the scaffolding 1 and enclosed by the thermally insulative cover 8. The at least one heating lamp 15 may be positioned within this defined area by a variety of mounts. The preferred embodiment of the present invention, however, comprises at least one suspension rod 29 and at least one first hook 30, as seen in FIG. 5. The at least one suspension rod 29 allows the at least one heating lamp 15 to hang from the scaffolding 1 while preserving the structural integrity of the scaffolding 1. With the scaffolding 1 in a vertical orientation, only a single suspension rod of the at least one suspension rod 29 is needed to support the at least one heating lamp 15. With the scaffolding 1 in a horizontal orientation, preferably a couple of suspension rods of the at least one suspension rod 29 is needed to support the at least one heating lamp 15, as seen in FIG. 14. The couple of suspension rods of the at least one suspension rod 29 evenly distribute the weight of the at least one heating lamp 15 across the scaffolding 1. More specifically, the at least one suspension rod 29 is mounted across the scaffolding 1, adjacent to the second planar portion 13. The at least one first hook 30 connects the at least one heating lamp 15 to the scaffolding 1, in both the vertical orientation and the horizontal orientation. The at least one heating lamp 15 is in a vertical orientation when the scaffolding 1 is in a vertical orientation. Therefore, only an individual first hook 30 of the at least one first hook 30 is needed to suspend the at least one heating lamp 15 from the at least one suspension rod 29. Similarly, the at least one heating lamp 15 is in a horizontal orientation when the scaffolding 1 is in a horizontal orientation, and therefore a couple of first hooks of the at least one first hook 30 is needed to suspend the at least one heating lamp 15 from the corresponding couple of suspension rods of at least one suspension rod 29. The at least one heating lamp 15 is tethered to the at least one first hook 30, which is coupled onto the at least one suspension rod 29. This configuration allows the at least one heating lamp 15 to hang without coming into contact with the ground. In an alternate embodiment of the present invention, a second hook 31 connects the at least one heating lamp 15 to the scaffolding 1. The at least one heating lamp 15 is tethered to the second hook 31, which is coupled onto the scaffolding 1, shown in FIG. 6. In alternate embodiments of the present invention, the at least one heating lamp 15 may be tethered to the first hook 30 and the second hook 31 with a chain, a rope, or a variety of length-adjustable tethers.

Although the invention has been explained in relation to its preferred embodiment, it is to be understood that many other possible modifications and variations can be made without departing from the spirit and scope of the invention as hereinafter claimed.

What is claimed is:

1. A modular portable sauna tent comprising:
   a scaffolding;
   a thermally insulative cover;
   at least one heating lamp;
   a first supplementary thermal insulative panel;
   the thermally insulative cover comprising a first panel, a second panel, and an overlay panel;
   the overlay panel comprising a first planar portion, a second planar portion, a third planar portion;
   the thermally insulative cover being tensionably mounted over the scaffolding;
   the first panel being positioned adjacent to the overlay panel;

the second panel being positioned adjacent to the overlay panel, opposite to the first panel;
the first panel and the second panel being positioned parallel to each other;
the overlay panel being attached adjacent to the scaffolding in between the first panel and the second panel;
the overlay panel being positioned perpendicular to the first panel and the second panel;
the first planar portion being hingedly connected to the second planar portion;
the third planar portion being hingedly connected to the second planar portion, positioned opposite to the first planar portion;
the at least one heating lamp being mounted within the scaffolding;
the first supplementary thermal insulative panel being mounted within the scaffolding; and
the first supplementary thermal insulative panel comprising a slot traversing thereinto.

2. The modular portable sauna tent as claimed in claim 1 comprising:
the first planar portion and the third planar portion being positioned perpendicular to the second planar portion.

3. The modular portable sauna tent as claimed in claim 1 comprising:
the scaffolding comprising a first base frame, a second base frame, and a plurality of lateral posts;
the first base frame being terminally connected to each of the plurality of lateral posts;
the second base frame being terminally connected to each of the plurality of lateral posts, opposite the second base frame;
the plurality of lateral posts being positioned normal to the first base frame and the second base frame; and
the plurality of lateral posts being laterally distributed around the scaffolding.

4. The modular portable sauna tent as claimed in claim 3 comprising:
the first base frame comprising a plurality of base posts;
the plurality of base posts being arranged into an overall polygonal shape; and
each of the plurality of base posts being terminally connected to a corresponding vertex of the overall polygonal shape.

5. The modular portable sauna tent as claimed in claim 3 comprising:
the second base frame comprising a plurality of base posts;
the plurality of base posts being arranged into an overall polygonal shape; and
each of the plurality of base posts being terminally connected to a corresponding vertex of the overall polygonal shape.

6. The modular portable sauna tent as claimed in claim 3 comprising:
each of the plurality of lateral posts comprising a plurality of assembly rods; and
the plurality of assembly rods being serially attached to each other.

7. The modular portable sauna tent as claimed in claim 3 comprising:
the first base frame and the second base frame each comprise a plurality of base posts;
each of the plurality of base posts comprising a plurality of assembly rods;
the plurality of base posts being arranged into an overall polygonal shape; and
the plurality of assembly rods being serially attached to each other.

8. The modular portable sauna tent as claimed in claim 3 comprising:
the first panel, the second panel, the first planar portion, and the third planar portion being positioned around the plurality of lateral posts; and
the third planar portion being positioned adjacent the first base frame.

9. The modular portable sauna tent as claimed in claim 3 comprising:
at least one support post;
the at least one support post being connected in between an arbitrary lateral post and an adjacent lateral post, wherein the arbitrary lateral post and the adjacent lateral post are from the plurality of lateral posts; and
the at least one support post being positioned perpendicular to the arbitrary lateral post and the adjacent lateral post.

10. The modular portable sauna tent as claimed in claim 1 comprising:
at least one flooring layer;
the at least one flooring layer being mounted adjacent the scaffolding; and
the thermally insulative cover; being positioned external to the at least one flooring layer.

11. The modular portable sauna tent as claimed in claim 9 comprising:
a plurality of third fasteners;
the plurality of third fasteners being perimetrically distributed across a flooring layer; and
the plurality of third fasteners connecting the flooring layer to the scaffolding.

12. The modular portable sauna tent as claimed in claim 11, wherein the flooring layer is made of a bamboo material.

13. The modular portable sauna tent as claimed in claim 10 comprising:
a thermal backing layer; and
the thermal backing layer being positioned external to the thermally insulative cover.

14. The modular portable sauna tent as claimed in claim 1 comprising:
a second supplementary thermal insulative panel;
the second supplementary thermal insulative panel being mounted adjacent the scaffolding; and
the second supplementary thermal insulative panel being positioned external to the thermally insulative cover.

15. The modular portable sauna tent as claimed in claim 1 comprising:
a plurality of first fasteners; and
the first planar portion being peripherally attached to the scaffolding by the plurality of first fasteners.

16. The modular portable sauna tent as claimed in claim 1 comprising:
a plurality of second fasteners; and
the third planar portion being peripherally attached to the scaffolding by the plurality of second fasteners.

17. The modular portable sauna tent as claimed in claim 1 comprising:
a first binding; and
the first planar portion, the second planar portion, and the third planar portion being peripherally attached to the first panel by the first binding.

18. The modular portable sauna tent as claimed in claim 1 comprising:
a second binding; and the first planar portion, the second planar portion, and the third planar portion being peripherally attached to the second panel by the second binding.

19. The modular portable sauna tent as claimed in claim 1 comprising:
    a door-defining slit; and
    the door-defining slit traversing through the first panel.

20. The modular portable sauna tent as claimed in claim 19 comprising:
    a third binding; and
    the third binding being operatively integrated into the door-defining slit, wherein the third binding is used to open and close the door-defining slit.

21. The modular portable sauna tent as claimed in claim 1 comprising:
    at least one suspension rod;
    at least one first hook;
    the at least one suspension rod being mounted across the scaffolding, adjacent to the second planar portion;
    the at least one heating lamp being tethered to the hook; and
    the hook being coupled onto the at least one suspension rod.

22. The modular portable sauna tent as claimed in claim 1 comprising:
    a second hook;
    the at least one heating lamp being tethered to the hook; and
    the hook being coupled onto the scaffolding.

* * * * *